United States Patent
Zhou

(10) Patent No.: US 9,265,206 B2
(45) Date of Patent: Feb. 23, 2016

(54) METHOD OF PRODUCING HYBRID SEEDS FOR ANNUAL COTTON BY CULTIVATING PERENNIALLY

(76) Inventor: Ruiyang Zhou, Nanning (CN)

( * ) Notice: Subject to any disclaimer, the term of this patent is extended or adjusted under 35 U.S.C. 154(b) by 605 days.

(21) Appl. No.: 13/217,305

(22) Filed: Aug. 25, 2011

(65) Prior Publication Data

US 2011/0307969 A1 Dec. 15, 2011

Related U.S. Application Data

(63) Continuation of application No. PCT/CN2009/000213, filed on Feb. 27, 2009.

(30) Foreign Application Priority Data

Feb. 25, 2009 (CN) .......................... 2009 1 0078533

(51) Int. Cl.
*A01H 1/02* (2006.01)
*A01G 1/06* (2006.01)

(52) U.S. Cl.
CPC ... *A01H 1/02* (2013.01); *A01G 1/06* (2013.01)

(58) Field of Classification Search
USPC .......................................... 800/260, 274, 312
See application file for complete search history.

(56) References Cited

U.S. PATENT DOCUMENTS 5,038,518 A * 8/1991 Davis ............................ 800/274
2008/0016593 A1 * 1/2008 Gal-On et al. ................ 800/279

OTHER PUBLICATIONS

Rea. Plant Physiology 6(1): 193-196, 1931.*

* cited by examiner

*Primary Examiner* — Keith Robinson
(74) *Attorney, Agent, or Firm* — Matthias Scholl, PC; Mathias Scholl

(57) ABSTRACT

A method of producing hybrid seeds for annual cotton by cultivating perennially, including the steps of: 1) planting annual cotton parent strains for hybridization and identifying the natural wintering capability thereof; 2) for annual cotton parent strains incapable of wintering naturally, taking a perennial cotton capable of wintering naturally as a rootstock and the annual cotton incapable of wintering naturally as a scionwood for grafting, and carrying out the perennial root culture of the obtained grafted plant; for annual cotton parent strains capable of wintering naturally, directly planting the strains and carrying out the perennial root culture of seedling plants thereof, or carrying out the perennial root culture of grafted plants thereof obtained according to the above grafting method; and (3) hybridizing the seedling plants and/or the grafted plants to produce seeds in the year of planting and/or grafting and period of perennial cultivation.

15 Claims, No Drawings

METHOD OF PRODUCING HYBRID SEEDS FOR ANNUAL COTTON BY CULTIVATING PERENNIALLY

CROSS-REFERENCE TO RELATED APPLICATIONS

This application is a continuation of International Patent Application No. PCT/CN2009/000213 with an international filing date of Feb. 27, 2010, designating the United States, now pending, and further claims priority benefits to Chinese Patent Application No. 200910078533.0 filed Feb. 25, 2009. The contents of all of the aforementioned applications, including any intervening amendments thereto, are incorporated herein by reference.

BACKGROUND OF THE INVENTION

1. Field of the Invention

The invention relates to a method of producing hybrid seeds of crops, and more particularly to a method of producing hybrid seeds for annual cotton by cultivating perennially.

2. Description of the Related Art

Although the advantages of cotton hybridization is significant, almost all existing hybrid seeds are planted in main cotton production areas by artificial emasculation hybridization using annual upland cotton (*Gossypium hirsutum*) or annual *Gossypium barbadense* parent strain, or by hybridization of an annual male sterile line and a restorer line. The main disadvantages are summarized below:

1) land must be ploughed up annually, and parent strain seeds must be sowed and bred annually.
2) roguing for parental propagation and hybrid seed production must be carried out annually.
3) although it is easy to find a restorer line and form heterosis crosses by using a genic male sterile line, the sterile line is difficult to propagate. This could be achieved generally by hybridization of male sterile plants (genotype: msms) and fertile sister plants thereof with fertile hybrid gene (genotype: Msms) which are isolated from a dual-use genic male sterile line, and the seed collected from the sterile plants still represents 1:1 in male sterile plants and male fertile plants for propagation. Therefore, 50% of the male fertile plants in female parent area must be removed from the hybrid seed production field each year, which is a concentrated and labor-intensive work. As cotton has an indefinite inflorescence with long flowering period, once the temperature exceeds 35° C., some male sterile strains will produce small or micro amount of pollen, which will affect the purity of hybrid seeds. In addition, because of non-uniform distribution of fertile plants and sterile plants, often fertile plants have to be removed continuously. It not only causes a waste of land, but also increases seed production cost.
(4) Although backcrossing of a cytoplasmic male sterile line and maintainer line can maintain male sterility, most of the existing cytoplasmic male sterile lines has harknessii cytoplasm, in which the restorer line is less and the hybridization generation contains adverse effects of sterile cytoplasm. Other types of cytoplasmic male sterile lines are prone to have genetic drift due to years of generative propagation sexually, leading to occurrence of fertile plants in a sterile line.

In spite of the fact that artificial emasculation hybridization needs high investment and cost, since there is no other better methods for hybrid seed production, artificial emasculation hybridization is still a main method for hybrid seed production. To reduce the seed production costs, generation F2 is generally used in cotton production.

SUMMARY OF THE INVENTION

In view of the above-described problems, it is one objective of the invention to provide a method of producing hybrid seeds for annual cotton by cultivating perennially that is easy, convenient, cost-effective, and can be widely used.

To achieve the above objective, in accordance with one embodiment of the invention, there provided is a method of producing hybrid seeds for annual cotton by cultivating perennially, the method being carried out at climatic zones, terrains, or artificial conditions in winter with average temperature $\geq 10°$ C. and the minimum temperature $\geq 0°$ C. in the coldest month, and the method comprising the steps of:

1) planting annual cotton parent strains for hybridization and identifying the natural wintering capability thereof;
2) for annual cotton parent strains incapable of wintering naturally, taking a perennial cotton capable of wintering naturally as a rootstock and the annual cotton incapable of wintering naturally as a scionwood for grafting, and carrying out the perennial root culture of the obtained grafted plant; for annual cotton parent strains capable of wintering naturally, directly planting the strains and carrying out the perennial root culture of seedling plants thereof, or carrying out the perennial root culture of grafted plants thereof obtained according to the above grafting method; and
(3) hybridizing the seedling plants and/or the grafted plants to produce seeds in the year of planting and/or grafting and period of perennial cultivation.

In a class of this embodiment, the parent strains as the female parent and/or male parent usually presents high difficulty of propagating (such as a male sterile line) or difficulty in maintaining the characteristics of their female parent and/or male parent via generative propagation, hence the perennial root culture can reduce the difficulty and cost of hybrid seed production.

In a class of this embodiment, when the female parent is a dual-use genic male sterile line, fertile plants, semi-sterile plants, and hybrid plants are removed in a planting and/or grafting year.

In a class of this embodiment, when the female parent is a cytoplasmic male sterile line, roguing is needed in a planting and/or grafting year.

In a class of this embodiment, the wintering naturally refers to winter survival rate $\geq 75\%$.

Since annual cotton has a weak root system, the annual cotton parent strain capable of wintering naturally should be reseeded after between 3 and 5 years of planting and perennial root culture.

The perennial cotton comprises a perennial type of *Gossypium barbadense*, perennial type of upland cotton in wild strain, or others perennial cotton or hybrids thereof: the rootstock is the seedling plants of cotton or cotton plants.

In a class of this embodiment, the winter survival rate of the rootstock is 100%.

In a class of this embodiment, the rootstock has no adverse effects on growth, development, fertility, yield, and quality of scionwood.

In a class of this embodiment, anti-soil-borne-disease is required for the rootstock when it is planted in the field with cotton soil-borne-disease.

In a class of this embodiment, the scionwood is the seedling cotton plant or cotton buds, blastema after wintering naturally, or blastema in the grafted plants after wintering.

In a class of this embodiment, the following management measures can be adopted for perennial root culture:

1) a first year of cotton planting: the cultivation and management will be made in accordance with the local cultivation and management for sowing, planting density, and cultivation and management methods of annual cotton; row ratio of male parents to female parents is the same as that for annual cotton hybrid seed production;
2) a second year of cotton planting and years followed: robust buds are selected and developed into lateral branches after sprout germinates in early spring, and unnecessary buds removed in time; unnecessary buds are topped off, pruned, and erased in summer and autumn, and to fertilize and control pests as early as possible; in winter cotton field needs cultivation, banking up, and fertilization; in winter or early spring, to remove the closely spaced cotton plants and trim according to sub-tropical fruit tree pruning method.

The invention comprises perennial root culture of annual cotton parent strains, and the hybridization farming needs no annual seeding, land productionation, and rouging except for the first planting year of perennial root culture. The genic male sterile line requires no removal of fertile plants in female parent cultivation area during the period of perennial root culture with this method. The propagation cost of male sterile lines has been greatly reduced because perennial root culture makes all types of male sterile lines remain the sterile characteristics year by year. The invention does not only simplify the process of hybrid seed production, but also increase seed yield by 30% compared with that using conventional annual cotton for seed production because the perennial root cultured parent strains have longer flowering and fruiting period.

Through grafting annual cotton parent strains in perennial cotton plants, annual cotton parent strains incapable of wintering naturally can be cultivated perennially, and the disadvantages of annual cotton, for example, shallow root system and short perennial cultivating period, are all overcome. The grafted plants can maintain fertility, yield, and quality of species, in which taking the buds or blastema in cotton plants as a scionwood for grafting and perennial planting achieves an asexual propagation, thereby maintaining sterility, yield, and quality of species.

In addition, the method used in the invention is applicable to average temperature ≥10° C. in the coldest month. Thus, the perennial cotton farming is extended northward from tropics to the southern or northern subtropical zone, and can be generalized in a wide range. Because the southern or northern subtropical zone has become a cotton-producing area with little cotton-planting zone, it is easy for distance separation and improve the purity of hybrid seeds. Furthermore, it is abundance of insects in the zones, which is beneficial for insect pollination and enhancing the hybrid seed yield.

DETAILED DESCRIPTION OF THE EMBODIMENTS

For further illustrating the invention, experiments detailing a method of producing hybrid seeds for annual cotton by cultivating perennially are described below. It should be noted that the following examples are intended to describe and not to limit the invention.

Example 1

After planting evaluation of the year 2004, the natural wintering survival rate of the genic male sterile plant of "Dong A" (a brand name of male sterile lines from Hubei Provincial Seed Group Co., Ltd) of *Gossypium hirsutum* in Nanning, Guangxi (average temperature in January was 14.1° C. and the lowest temperature was 5.6° C.) had been over 95.5%, while that of fertile sister plants thereof had been 65% (the fertile plants had to be totally removed for the purpose of seed production, therefore the low wintering rate did not affect hybrid seed production); the natural wintering survival rate of a restorer line thereof, i.e., Guoshenhan 284 (a brand name of restorer lines), was 75% (due to tall plants in the next planting year, the density should be sparse, so 75% of wintering rate was sufficient), in the next year and the third year was 100%, in the fourth year (i.e. 2008) was 0.

During 2004 to 2007, perennial cultivation of "Dong A" and Guoshenhan 284 was directly conducted in Nanning, Guangxi and planted/managed according to local cultivation time, planting density, and cultivation/management methods of annual cotton. In wintering period of the first cotton planting year, i.e., in January of the second year, cultivation, banking up, and organic fertilizer were applied in cotton fields. Closely spaced cotton plants and fertile plants of Dong A were removed. The plants were trimmed off according to sub-tropical fruit tree pruning method. Generally the trunk was around between 80 and 100 cm in height. The weak and diseased branches were cut off and 2-3 robust branches remained. If the branches were too weak, leave the trunk while cutting off all other lateral branches. From the second year of cotton planting, the cotton reached perennial root culture phase. January to February of each year was the wintering period for perennial cotton, when cotton grew slowly or stopped growing. In January, cultivation, banking up, and applied organic fertilizer were carried out in cotton fields. To remove closely spaced cotton plants and trim according to sub-tropical fruit tree pruning method. It was the growing season for perennial cotton from March to December. It should be noted to choose around 3 robust buds to develop into lateral branches and remove unnecessary buds in time in early spring; to top off, prune, and erase unnecessary buds in summer and autumn, and maintain sufficient air and light. Since perennial cotton had high yield, it needed repeated fertilization and meantime control pests as early as possible.

Afterwards, take perennial or annual male sterile line of "Dong A" as female parent strains, and take perennial or annual restorer line of Guoshenhan 284 as male parent strains with a row ratio of male parent: female parent 1:4. The hybridized cotton seed yield of perennial sterile line×perennial restorer line, perennial sterile line×annual restorer line, and annual sterile line×annual restorer line were compared respectively. Studies showed that when both male and female parent were perennial, there were three boll formation peaks; when both male and female parent were annual, there were only two boll formation peaks. Compared with that of the latter (both male and female parent were annual), seed yield of the former (both male and female parent were perennial) had been increased by 32%, amount of labor used decreased by 22%, and there were no seed cost and the hybrid seed production cost was reduced by approx. 54% per unit weight. Perennial male sterile line×annual restorer line had the same seed yield as that of annual sterile line×annual restorer line, but the hybrid seed production cost had been decreased by about 12%. The yield and quality of hybridized generations of perennial male sterile lines crossover with a male parent had no significant difference compared with that of hybridized generations of annual male sterile lines crossover with the same male parent. Therefore, perennial cultivation was a good method for hybrid seed production to increase yield, decrease labors, and reduce cost.

The sterile plants "Dong A" required re-seeding after 3-5 years of planting, and the restorer line Guoshenhan 284 also needed re-seeding after 3 years of planting.

Example 2

In 2005, take wintering blastema of the sterile line "Dong A" described in Example 1 and the restorer line Guoshenhan 284 as a scionwood and take pengpeng cotton (a perennial cotton in Hainan Island) and perennial sea-island cotton (a perennial cotton in Hainan Island) as s rootstock for grafting. The grafted plants were cultured and the wintering rate thereof measured, which was 100% for 4 consecutive years after surviving the coldest winter in January, 2008. The grafted plants were cultured perennially for hybrid seed production, which increased seed yield and reduced production costs.

Example 3

Studies showed that "Dong A" dual-use genic male sterile line of Gossypium hirsutum and H04A dual-use genic male sterile line of Gossypium barbadense (selected by Guangxi University) had the natural wintering rates of 95.5% and 92.3%, respectively in 2004 in Nanning, Guangxi Province. A grafting combination experiment was conducted in 2004 in Nanning, Guangxi (average temperature in January was 14.1° C. and the lowest temperature was 5.6° C.) by using four types of rootstocks and two grafted male sterile line scionwoods. The resulting eight grafting combinations were hybridized with a restorer line to produce hybrid seeds. The two scionwoods were: A. seed shoots of "Dong A" dual-use genic male sterile line of Gossypium hirsutum (from Hubei Provincial Seed Group Co., Ltd in 2004); B. seed shoots of H04A dual-use genic male sterile line of annual Gossypium barbadense. Studies showed that both scionwood A and scionwood B could not remain 100% natural wintering rate in Nanning.

Four rootstocks were: A. Pengpeng cotton (a perennial cotton in Hainan Island); B. Perennial sea-island cotton (a perennial cotton in Hainan Island); C. Hybrid seed F1 of upland cotton cytoplasmic male sterile line P2001A (from Hubei Academy of Agricultural Science)×pengpeng cotton (ditto for source); D. Hybrid seed F1 of P2001A (ditto for source)×perennial sea-island cotton (ditto for source). Studies showed that 100% of the four rootstock materials had been wintering normally for six consecutive years in Nanning, and the adult plants had survived 0° C. in artificial climate chamber, which indicated that they could endure low temperature of 0° C. for 5 consecutive days. Through the test of these rootstock materials, it was found out that the rootstocks were resistant to fusarium wilt and verticillium wilt.

On Mar. 7, 2004, seeds for rootstocks and scionwoods were sowed in Nanning. The rootstocks were cultured in nutrient cups while the scionwood in nursery seedbeds. Once the rootstocks had grown their own euphylla, the scionwoods were grafted. The grafted plants were placed in a small shed covered with plastic films for warm and moisture keeping. The plastic film was uncovered when the graft union has sealed 6 days after grafting. The seedlings were hardened for 2 days under a shade net. The successfully grafted and robust seedlings were transplanted to a big field for perennial cultivation. Perennial cultivation method was the same as that in the Example 1.

On Feb. 15, 2006, the restorer line Guoshenhan 284 was sowed earlier and seedlings were cultured in nutrition cups of a vinyl house. When the temperature was suitable for cotton cultivation, they were transplanted to the field. The row ratio of female parent (grafted sterile plants of the above eight combinations of grafted male sterile line) to male parent (restorer line Guoshenhan 284) was 1:4. High fertilizer water management measures were employed to promote growth to make reproductive period close to the grafted plants and increase seed yield. The above eight combinations of grafted plants crossover with restorer lines had increased hybrid seed yield by 10% than the normal sowing of annual male sterile line×annual restorer line in March of that year.

In January 2008, Nanning had suffered the most serious cold weather in history. From January 14 to February 5, the average temperature was below 10° C. for 23 consecutive days, average daylight temperature was below 5° C. for 7 days, the lowest temperature was below 5° C. for 13 days, the extreme lowest temperature was 1.6° C., and monthly mean temperature was 9.8° C. However, the four rootstocks still had 100% survival rate, and the grafted plants of the above eight grated combinations had 100% survival rate after baptism of cold weather in Nanning in January 2008, while the ungrafted "Dong A" and H04A self-rooted control plants were all dead due to the cold weather.

Studies on the eight grafting combinations of the above 4 kinds of rootstock with 2 kinds of sterile scions showed that, all grafted rootstocks and scionwoods had great affinity and no specificity existed in the rootstocks and scions. All the rootstocks had no adverse effects on economics, yield, and quality of scionwoods. Until January 2009, the grafted plants of the above eight grafting combinations had been cultivated for 5 consecutive years, survive winter by 100%, grew normally, no fertile plants separated, and hybrid seed production can be carried out continually. Thus, it significantly reduced the propagation cost of male sterile lines and simplified the procedure of hybrid seed production.

Example 4

Studies showed that GA5 (from Institute of Industrial Crops of Sichuan Academy of Agricultural Science), a dual-use genic male sterile line, could not survive the winter normally in Hubei and thus it was annual cotton. In 2006 in Gong'an County of Hubei Province, take perennial sea-island cotton (a perennial cotton in Hainan Island) as a rootstock to propagate the dual-use genic male sterility line GA5 using a grafting method. The fertile plants were removed in the flowering period. The grafting plants were keep warm every winter with a vinyl house, in which the average temperature greater than or equal to 10° C. in January, for safe wintering and to establish an original parent garden for genic male sterile lines in the main cotton producing areas. Perennial cultivation method was the same as that in Example 1.

In 2007 and 2008, take the above perennial sea-island cotton as a rootstock and the blastema of wintering plants in the original parent garden for genic male sterile line GA5 as a scionwood, drafted plants were collected and cultured every year. Meanwhile, seedling plants of restorer line Guoshenhan 284 by seed propagating were cultured for hybridization. Thus, hybrid seed technology system of male sterile line using vinyl house for overwintering and annual restorer line had been established. The advantage was that hybrid seed production could be carried out directly in main cotton producing areas, and could reduce technique consultant and seed transport costs; while the disadvantage was that propagating of sterile lines and restorer lines had to be conducted.

INDUSTRIAL PRACTICABILITY

Hybrid seed production method of cotton provided in the invention can achieve consecutive perennial cultivation of annual cotton parent strains for hybrid seed production. It does not need seeding, land preparation, and roguing every year in perennial cultivation, especially for propagating of cotton male sterile lines. As it does not need restorer lines and plants can grow for many years, thereby greatly reducing the cost of hybrid seed production and improving seed yield during perennial cultivation period. Using the method of the invention, hybrid seed production procedures are greatly simplified, seed production costs decreased, and seed yield increased. In addition, the method of the invention has a wide range of application; it only requires the average temperature ≥1° C. in the coldest month and the lowest temperature ≥0° C. Thus, the method is suitable for tropical and southern subtropical regions. In conclusion, the method of the invention has excellent industrial practicability in hybrid seed production of cotton.

The invention claimed is:

1. A method of producing hybrid seeds for annual cotton by cultivating perennially, the method comprising:
   a) growing annual cotton parent strains, the annual cotton parent strains comprising a female parent plant and a male parent plant, the female parent plant being a genic male sterile line;
   b) forming rootstocks using a perennial cotton species, the perennial cotton species having a winter survival rate of 100% in a condition having an average winter temperature higher than 10° C. and having a minimum winter temperature higher than 0° C.;
   c) grafting the annual cotton parent strains obtained in a) as scions onto the rootstocks obtained in b) to form a perennial union of the female parent plant and a perennial union of the male parent plant, respectively, wherein the perennial union of the female parent plant produces male sterile flowers every year during perennial cultivation;
   d) cultivating the perennial union of the female parent plant and the perennial union of the male parent plant obtained in c) perennially in the condition having the average winter temperature higher than 10° C. and having the minimum winter temperature higher than 0° C.; and
   e) cross pollinating the perennial union of the female parent plant and the perennial union of the male parent plant obtained in d) to produce hybrid seeds.

2. The method of claim 1, wherein the perennial cotton species is a perennial type of *Gossypium barbadense* or a perennial type of wild upland cotton.

3. The method of claim 1, wherein a) is performed by sowing seeds of the annual cotton parent strains to produce seedlings.

4. The method of claim 3, wherein c) is performed by grafting the seedlings obtained in a) as scions onto the rootstocks obtained in b) to form a perennial union of the female parent plant and a perennial union of the male parent plant.

5. The method of claim 1, wherein a) is performed by growing the annual cotton parent strains to produce cotton buds.

6. The method of claim 5, wherein c) is performed by grafting the cotton buds obtained in a) as scions onto the rootstocks obtained in b) to form a perennial union of the female parent plant and a perennial union of the male parent plant.

7. The method of claim 1, wherein a) is performed by:
   planting the annual cotton parent strains in an condition having an average winter temperature higher than 10° C. and having a minimum winter temperature higher than 0° C.;
   cultivating the annual cotton parent strains to winter over; and
   cultivating the annual cotton parent strains after wintering to produce blastemas.

8. The method of claim 7, wherein c) is performed by grafting the blastemas obtained in a) as scions onto the rootstocks obtained in b) to form a perennial union of the female parent plant and a perennial union of the male parent plant.

9. A method of producing hybrid seeds for annual cotton by cultivating perennially, the method comprising:
   a) providing a female parent plant of annual cotton, the female parent plant being a genic male sterile line, and removing fertile plants, semi-sterile plants, and hybrid plants from the female parent plant;
   b) providing a male parent plant of annual cotton, the male parent plant having a winter survival rate equal to or higher than 75% in a condition having an average winter temperature higher than 10° C. and having a minimum winter temperature higher than 0° C.;
   c) growing the female parent plant to produce a scion;
   d) forming a rootstock using a perennial cotton species, the perennial cotton species having a winter survival rate of 100% in the condition having the average winter temperature higher than 10° C. and having the minimum winter temperature higher than 0° C.;
   e) grafting the scion obtained in c) onto the rootstock obtained in d) to form a perennial female parent union, wherein the perennial female parent union produces male sterile flowers every year during perennial cultivation;
   f) cultivating the male parent plant and the perennial female parent union in the condition having the average winter temperature higher than 10° C. and having the minimum winter temperature higher than 0° C.; and
   g) cross pollinating the male parent plant and the perennial female parent union to produce hybrid seeds.

10. The method of claim 9, wherein the female parent plant has a winter survival rate lower than 75% in the condition having the average winter temperature higher than 10° C. and having the minimum winter temperature higher than 0° C.

11. The method of claim 9, wherein c) is performed by sowing a seed of the female parent plant to produce a seedling.

12. The method of claim 11, wherein e) is performed by grafting the seedling obtained in c) onto the rootstock obtained in d) to form a perennial female parent union.

13. The method of claim 9, wherein c) is performed by growing the female parent plant to produce a cotton bud.

14. The method of claim 13, wherein e) is performed by grafting the cotton bud obtained in c) onto the rootstock obtained in d) to form a perennial female parent union.

15. The method of claim 1, wherein a) further comprises removing fertile plants, semi-sterile plants, and hybrid plants from the female parent plant.

* * * * *